United States Patent [19]

Arnstein et al.

[11] Patent Number: 4,736,624

[45] Date of Patent: Apr. 12, 1988

[54] CONSISTOMETER FOR ANALYSIS OF RHEOLOGICAL CHANGE

[75] Inventors: Rodolphe Arnstein, Boulogne; Patrick Bisson, Les Ulis; Marc P. Blaquiere, St. Remy les Chevreuse, all of France

[73] Assignee: Total Compagnie Francaise des Petroles, Paris, France

[21] Appl. No.: 13,498

[22] Filed: Feb. 11, 1987

[30] Foreign Application Priority Data

Feb. 27, 1986 [FR] France .................. 86 02701

[51] Int. Cl.⁴ .......................................... G01N 11/14
[52] U.S. Cl. ......................................... 73/59
[58] Field of Search ................................ 73/59, 60

[56] References Cited

U.S. PATENT DOCUMENTS

| | | | |
|---|---|---|---|
| 4,466,276 | 8/1984 | Ruyak et al. | 73/59 |
| 4,524,611 | 6/1985 | Richon et al. | 73/59 |
| 4,534,209 | 8/1985 | Sanders | 73/59 |
| 4,633,708 | 1/1987 | Blommaert | 73/59 |

*Primary Examiner*—Stewart J. Levy
*Assistant Examiner*—Joseph W. Roskos
*Attorney, Agent, or Firm*—Sughrue, Mion, Zinn, Macpeak and Seas

[57] ABSTRACT

A consistometer usable at a work site comprises a stationary receptacle (9) which is placed in an enclosure (3) defined by a consistometer casing (2) and is provided with a stirrer (17) with a rotary drive spindle (18). The casing has an extension (20) in which there is arranged an intermediate shaft (23) angularly fast with a torque receiver (22) of a magnetic type actuated from outside the extension by a driven torque transmitter (21). Shaft (23) is angularly fast with a coupling device (24) for engagement with the spindle simply by the spindle being introduced into the coupling device when the receptacle is placed in the casing.

8 Claims, 3 Drawing Sheets

CONSISTOMETER FOR ANALYSIS OF RHEOLOGICAL CHANGE

BACKGROUND OF THE INVENTION

The present invention relates to consistometers comprising an enclosure in which there is installed a receptacle for receiving a rheologically changing material such as, for example, a cement slag, and which is capable of receiving a fluid under pressure transmitted to the material by a membrane closing the receptacle, while measuring equipment enables the rheological change of the material to be studied.

These instruments are heavy and bulky. They are installed in laboratories but are not suitable for use at a work site.

SUMMARY OF THE INVENTION

According to the invention there is provided a consistometer comprising a casing of generally cylindrical shape forming a consistometer enclosure which is arranged vertically and is open at its upper part, an upper plug adapted to be screwed on to the upper part to close it, means for introducing a fluid under pressure into the enclosure, an elongate receptacle for receiving a rheologically changing material, in the shape of a body of revolution, provided with closing means at its two ends, partially bounded by an elastic membrane and adapted to be installed vertically in the enclosure, a paddle stirrer adapted to be placed in the receptacle and provided with a driving spindle, a shaft bearing in the closing means for closing the lower end of the receptacle to allow the spindle to pass therethrough in a leakproof manner, drive means arranged outside the casing for driving the spindle in rotation, and means for measuring the driving torque of the spindle. The casing comprises, in its lower part, an extension in which there is arranged vertically an intermediate shaft for transmitting rotary motion and which is provided with a torque receiving member of a torque transmission system of the magnetic type and for interacting with a torque transmitting member outside the extension and which is driven by the drive means, said intermediate shaft being mechanically linked at its upper end to a mechanical coupling device adapted to engage with the lower end of the spindle as the spindle descends when the receptacle is placed in the consistometer enclosure and is adapted to be disengaged therefrom as the spindle is raised again when the receptacle is withdrawn from the enclosure.

All connections between the interior and the exterior of the consistometer enclosure can thus be avoided, other than connections permitting the introduction of a fluid under pressure into the enclosure and its removal therefrom. Thus, the problems of sealing or the friction which would be produced by the passage of a shaft through a wall separating a medium at a high pressure from the environment no longer exist. Furthermore, the means and the operations of making use of the receptacle can be more straightforward.

The torque transmission system of a magnetic type preferably comprises a permanent driving magnet which is fixed in rotation to the driving means and is provided outside the extension, and a driven permanent magnet fixed in rotation to said intermediate shaft and provided inside the extension.

A spring biassing the coupling device vertically away from the intermediate shaft is advantageously inserted between the coupling device and the intermediate shaft to compensate for changes in length of the spindle, mechanical means for reciprocal engagement ensuring that the coupling device and the intermediate shaft are fixed together in rotation.

The coupling device may comprise a vertical housing adapted to receive the spindle and laterally equipped with a stud biassed resiliently towards the inside of this housing, the spindle having in its lower end a vertical groove in which the stud is engageable.

A significant simplification can also be obtained by arranging for the means for closing the upper end of the receptacle to be provided by the upper plug. The receptacle may comprise for this purpose an outer collar which can be clamped against the upper plug by means of a clamping ring which is screwed internally on to the plug. The shaft bearing is advantageously rigidly carried by a lower plug which is adapted to be screwed into the lower end of the receptacle, enabling the receptacle to be filled, by removing the lower plug and by fastening the receptacle to the upper plug, the receptacle-upper plug assembly being inverted in relation to the position which is later to be adopted in the consistometer.

The upper end of the spindle may be held by a pivot arranged in the upper plug.

The elastic membrane should not interfere with the rigidity of the receptacle and it must, in particular, be disconnected from the points of bearing of the spindle. Side openings may advantageously be provided in the receptacle, together with an annular elastic membrane capable of being clamped on to the receptacle to close the side openings.

DETAILED DESCRIPTION OF THE PREFERRED EMBODIMENT

Figure 1:
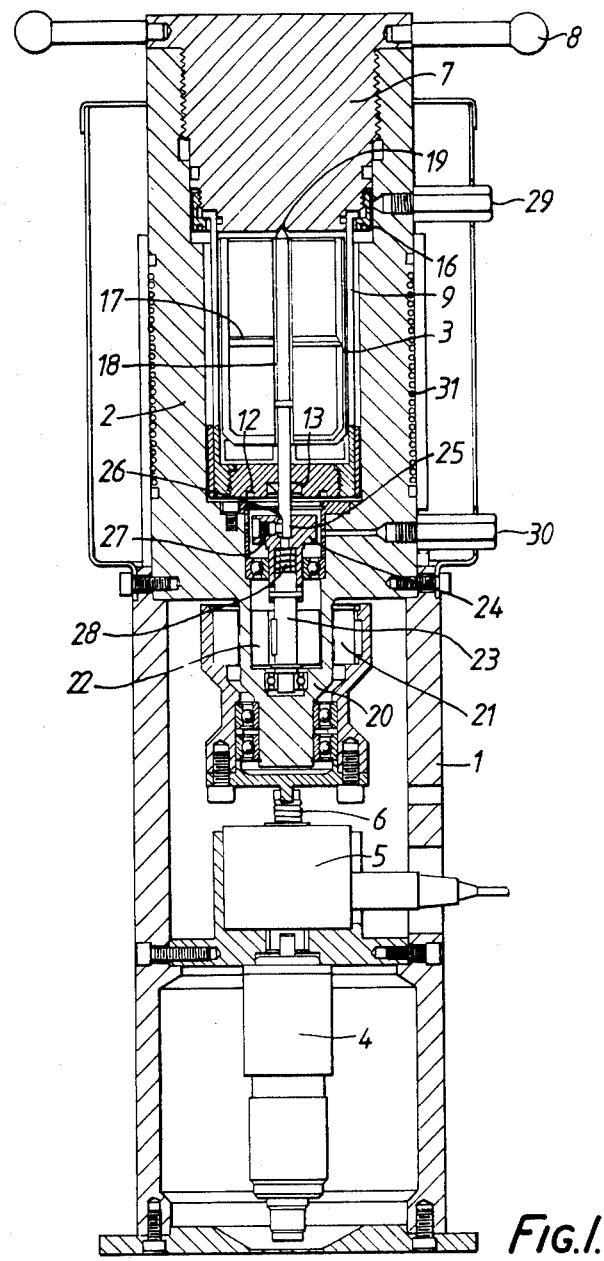
FIG. 1 shows, in elevation and partial section, an overall view of a consistometer.

The consistometer shown in FIG. 1 comprises a framework 1 which supports a casing 2 of generally cylindrical shape, made of a non-magnetic material, such, for example, as aluminium or an aluminium alloy, internally defining a consistometer enclosure 3, and housing a motor with a speed reducer 4 driving a drive shaft 6 via a torquemeter 5.

The enclosure 3 is closed at its upper part by an upper plug 7 which can be screwed into the casing 2 by means of demountable handles 8.

Figure 2:
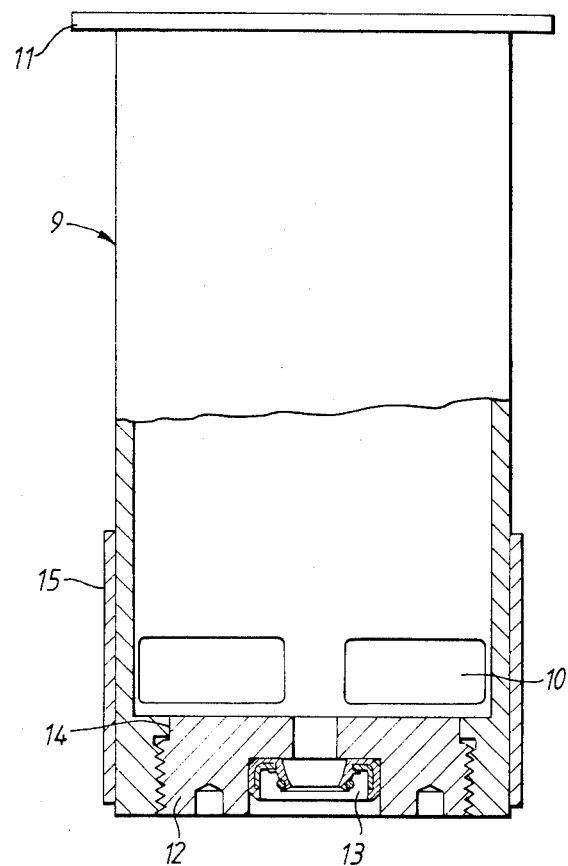
FIG. 2 is an elevation view, with sectioning of the lower part, of a receptacle for a rheologically changing material used in the consistometer of FIG. 1.
Figure 3:
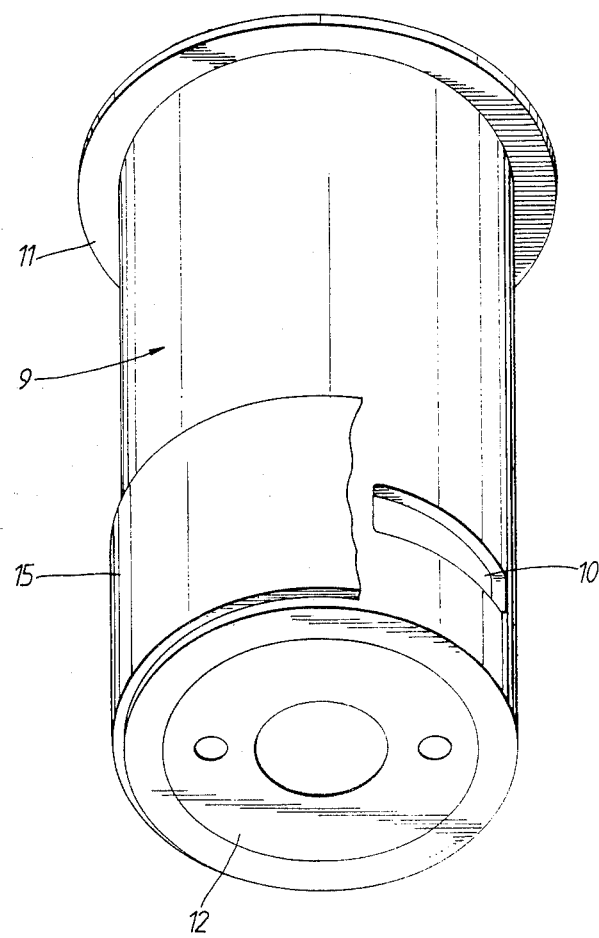
FIG. 3 is a perspective view of the receptacle of FIG. 2.

The upper plug 7 carries an elongate receptacle 9 for a rheologically changing material, which is made of aluminium alloy, and which can be seen better in FIGS. 2 and 3. The receptacle 9 has the shape of a body of revolution, e.g. a cylinder, for example of 60 mm bore, whose side wall is provided with openings or windows 10, whose open upper end carriers a collar or flange 11 and whose lower end is closed by a lower plug 12. Plug 12 may be screwed into the side wall of the receptacle 9, into a reinforced section of this wall. In its centre, the plug 12 carries a rotary shaft seal 13, for example a Paulstra type IE seal. Satisfactory centering of the plug 12 and, consequently, of the shaft seal 13 is produced by a bearing 14 provided at the end of the plug threading, which engages in a corresponding cavity in the wall of the receptacle 9.

A cyclindrical ring 15 made of an elastomer such as the product sold under the name of Viton, for example 2 mm in thickness, is drawn like a sleeve on to the side wall of the receptacle 9 to close the windows 10.

The receptacle 9 is fastened to the upper plug 7 by clamping the collar 11 against the plug by means of a fast-screw ring 16, as can be seen in FIG. 1. The receptacle 9 contains a stirrer 17 carried by a driving spindle 18 which passes through the shaft seal 13 and extends downwards out of the receptacle 9 and which bears with its upper end on a pivot 19 arranged in the upper plug 7.

The casing 2 is extended downwards by a central extension 20. Outside this extension 20 and around it there is arranged a driving permanent magnet 21, linked in rotation with the driving shaft 6. A driven permanent magnet 22 which is integrally fixed in rotation to an intermediate transmission shaft 23 bearing a coupling device 24 is arranged inside the extension 20 and facing the driving magnet 21. The extension 20 is used to support bearings for these two magnets 21 and 22.

The coupling device 24 comprises a housing 25 intended to receive the lower end of the spindle 18. The lower end of the spindle is laterally provided with a vertical groove 26 into which a lateral stud 27 can extend. Stud 27 is carried by the coupling device 24 and biassed by a spring inwardly of the housing 25. Thus, when the lower end of the spindle 18 is lowered into the housing 25, the stud 27 engages in the groove 26. Thus, automatic latching occurs when the upper plug 7 and the receptacle 9, which is stationary, are simply placed in position.

Provision is made for vertical play to be taken up to ensure that the upper end of the spindle 18 is retained in the pivot 19. For this purpose, while the coupling device 24 is angularly fast with the intermediate shaft 23, it can move vertically relative to the shaft 23, a spring 28 biassing the device 24 upwardly to compensate for changes in length of the spindle 18.

The introduction of a fluid under pressure into the enclosure 3 and its withdrawal are achieved by means of lines 29 and 30. Heating is carried out by means of a heater element 31 embedded in the outside of the casing 2. A pressure of 1,000 bars and a temperature of 200° C. can be attained.

When a test is to be carried out, the procedure may be as follows. The stirrer 17 is placed in the receptacle 9 and the assembly is fastened to the upper plug 7 by screwing up the ring 16 using a special key. The membrane 15 is pulled on to the receptacle 9, care being taken to leave a similar length on each side of the windows 10, and the receptacle 9 is inverted and filled, for example with cement slag. The lower plug 12 is slipped on to the spindle 18 by placing the point of the spindle 18 in the pivot 19, and then the lower plug 12 is screwed on the the receptacle 9 using a special key. The assembly of the upper plug 7 and of the closed receptacle 9, to which it is fastened, is then inverted and introduced into the consistometer enclosure 3. By screwing the upper plug 7 on to the casing 2 using the handles 8, the receptacle 9 and the spindle 18, whose lower end automatically engages in the coupling device 24, are placed in working position.

During the test, the stirrer 17 is driven at a constant speed, for example at 150 revolutions/minute. The temperature and the pressure can be varied according to a programme; in the case of a cement slag for well drilling, this programme is specified in accordance with the API standards.

The change in the driving torque measured by the torquemeter 5 is recorded as a function of time in order to determine the setting time of the slag. Instead of using the torquemeter 5, it would also be possible to measure the current of the motor 4, but the measurement of the consistency of the slag performed in this manner would be less accurate.

There is thus provided a consistometer having a simplified construction, the use of which can be universal, but which retains good accuracy of measurement. The consistometer also permits a reduction of the time and, consequently, the cost of the handling operations preceding and following the measurement period as such. The rotary stirrer is automatically placed in a working position as soon as it is installed in the consistometer enclosure and is coupled without mechanical contact to means for driving the stirrer in rotation and for measuring the drive torque which are located outside the enclosure.

What is claimed is:

1. A consistometer, comprising: a casing (2) of generally cylindrical shape forming a consistometer enclosure (3) which is arranged vertically and is open at its upper part, an upper plug (7) adapted to be screwed on to said upper part to close it, means (29,30) for introducing a fluid under pressure into said enclosure, an elongate receptacle (9) for receiving a rheologically changing material, in the shape of a body of revolution, provided with closing means (7,11,12) at upper and lower ends thereof, partially surrounded by an elastic membrane (15) and adapted to be installed vertically and non-rotatably in said enclosure, a rotatable paddle stirrer (17) adapted to be placed in said receptacle and provided with a driving spindle (18), a shaft seal (13) in said lower end closing means for closing the lower end of said receptacle to allow said spindle to pass therethrough in a leakproof manner, drive means (4,6) arranged outside said casing for driving said spindle in rotation, and means (5) for measuring the driving torque of said spindle, wherein said casing comprises, in its lower part, an extension (20) in which there is arranged vertically an intermediate shaft (23) for transmitting rotary motion and which is provided with a torque receiving member (22) of a torque transmission system of the magnetic type and for interacting with a toque transmitting member (21) outside said extension, driven by said drive means, said intermediate shaft being mechanically linked at its upper end to a mechanical coupling device (24) adapted to engage with the lower end of said spindle as said spindle descends when said receptacle is placed in said consistometer enclosure and adapted to be disengaged therefrom as said spindle is raised again when said receptacle is withdrawn from said enclosure.

2. A consistometer according to claim 1, wherein said torque transmission system of the magnetic type comprises a driving permanent magnet (21) outside said extension and fixed in rotation to said drive means, and a driven permanent magnet (22) inside said extension and fixed in rotation to said intermediate shaft.

3. A consistometer according to claim 1, wherein a spring (28) is inserted between said coupling device and said intermediate shaft to permit relative vertical movement thereof, said coupling device and said intermediate shaft being fixed together in rotation.

4. A consistometer according to claim 1, wherein said coupling device comprises a vertical housing adapted to receive said spindle and provided laterally with a stud (27) resiliently biassed towards the inside of said housing, said spindle having at its lower end a vertical groove (26) in which said stud is engageable.

5. A consistometer according to claim 1, wherein, at its upper part, said receptacle comprises an outer collar (11) adapted to be clamped against said upper plug which thus forms said closing means for closing said upper end of said receptacle.

6. A consistometer according to claim 5, wherein said means for closing said lower end of said receptacle comprises a lower plug (12) adapted to be screwed on to said receptacle.

7. A consistometer according to claim 5, wherein a pivot (19) is provided in said upper plug for receiving the upper end of said spindle.

8. A consistometer according to claim 1, wherein said receptacle comprises lateral openings (10) and said elastic membrane comprises an annular ring (15) adapted to clamp on to said receptacle to close said lateral openings.

* * * * *